US012806159B2

(12) United States Patent
Pisak

(10) Patent No.: US 12,806,159 B2
(45) Date of Patent: Nov. 24, 2026

(54) PHARMACEUTICAL COMBINATIONS FOR THE TREATMENT OF PAIN

(71) Applicant: IMUNEKS FARMA ILAC SANAYI VE TICARET A.S., Istanbul (TR)

(72) Inventor: Mehmet Nevzat Pisak, Besiktas/Istanbul (TR)

(73) Assignee: IMUNEKS FARMA ILAC SANAYI VE TICARET A.S., Istanbul (TR)

( * ) Notice: Subject to any disclaimer, the term of this patent is extended or adjusted under 35 U.S.C. 154(b) by 956 days.

(21) Appl. No.: 17/289,593

(22) PCT Filed: Oct. 16, 2019

(86) PCT No.: PCT/TR2019/050872

§ 371 (c)(1),
(2) Date: Apr. 28, 2021

(87) PCT Pub. No.: WO2020/091711

PCT Pub. Date: May 7, 2020

(65) Prior Publication Data

US 2021/0393553 A1 Dec. 23, 2021

(51) Int. Cl.

*A61K 31/138* (2006.01)
*A61K 31/192* (2006.01)
*A61K 31/196* (2006.01)
*A61P 29/00* (2006.01)

(52) U.S. Cl.

CPC .......... *A61K 31/138* (2013.01); *A61K 31/192* (2013.01); *A61K 31/196* (2013.01); *A61P 29/00* (2018.01)

(58) Field of Classification Search

CPC ..... A61P 29/00; A61K 31/138; A61K 31/192; A61K 31/196

See application file for complete search history.

(56) References Cited

U.S. PATENT DOCUMENTS

| | | | | |
|---|---|---|---|---|
| 2006/0142288 A1* | 6/2006 | Peroutka | A61K 31/537 514/569 |
| 2009/0117197 A1* | 5/2009 | Bascomb | A61K 31/407 514/415 |
| 2017/0035787 A1 | 2/2017 | Trieu | |

FOREIGN PATENT DOCUMENTS

| | | | |
|---|---|---|---|
| CN | 101310725 A * | 11/2008 |
| EP | 1011658 B1 | 12/2005 |
| EP | 2014284 A1 | 1/2009 |
| EP | 2175861 B1 | 8/2014 |
| WO | WO 2009/154944 A2 | 12/2009 |

OTHER PUBLICATIONS

Light KC, Bragdon EE, Grewen KM, Brownley KA, Girdler SS, Maixner W. Adrenergic dysregulation and pain with and without acute beta-blockade in women with fibromyalgia and temporomandibular disorder. J Pain. May 2009;10(5):542-52. doi: 10.1016/j.jpain.2008.12.006. PMID: 19411061; PMCID: PMC2700184. (Year: 2009).*
Ting Zhou, Kaixiang Yang, Sudip Thapa, Huiquan Liu, Bangyan Wang, Shiying Yu, Differences in Symptom Burden Among Cancer Patients With Different Stages of Cachexia, Journal of Pain and Symptom Management, vol. 53, Issue 5, pp. 919-926, ISSN 0885-3924, https://doi.org/10.1016/j.jpainsymman.2016.12.325 (Year: 2017).*
Nonsteroidal Anti-Inflammatory Drugs (NSAIDs) (Therapeutic Class Overview/Summary, University of Massachusetts Medical School, Jan. 25, 2016, retrieved from: https://www.medicaid.nv.gov/Downloads/provider/Nonsteroidal%20Anti-Inflammatory%20Drugs%20(NSAIDs).pdf). (Year: 2016).*
Shinde et al., "Efficacy and Safety of Oral Diclofenac Sustained release Versus Transdermal Diclofenac Patch in Chronic Musculoskeletal Pain: A Randomized, Open Label Trial", 2017, Journal of Pharmacology and Pharmacotherapeutics, 8, pp. 166-171 (Year: 2017).*
Tchivileva et al., "Effect of catechol-O-methyltransferase polymorphism on response to propranolol therapy in chronic musculoskeletal pain: A randomized, double-blind, placebo-controlled, crossover pilot study", 2010, Pharmacogenetic Genomics, 20, pp. 239-248 (Year: 2010).*
Lopressor, "Lopressor (metoprolol tartrate) tablet", 2008, U.S. Food and Drug Administration, pp. 1-10 (Year: 2008).*
Inderal, "Inderal (propranolol hydrochloride) Tablets", 2010, U.S. Food and Drug Administration, pp. 1-18 (Year: 2010).*
Chaudhari et al., "Pharmaceutical Excipients: A review", 2012, International Journal of Advances in Pharmacy, Biology and Chemistry, 1, pp. 21-34 (Year: 2012).*
Hawken et al., "Successful Use of Propranolol in Migraine Associated With Electroconvulsive Therapy", 2001, Headache, 41, pp. 92-96 (Year: 2001).*
Zencirci, "Comparison of the effects of dietary factors in the management and prophylaxis of migraine", 2010, Journal of Pain Research, 3, pp. 125-130 (Year: 2010).*
Craft et al., Sex differences in pain and analgesia: the role of gonadal hormones. Eur J Pain. Oct. 2004;8(5):397-411.
International Search Report and Written Opinion for PCT/TR2019/050872. Mailed Mar. 31, 2020. 8 pages.
Merry et al., Combined acetaminophen and ibuprofen for pain relief after oral surgery in adults: a randomized controlled trial. Br J Anaesth. Jan. 2010;104(1):80-8.
Valdes et al., Association of Beta-Blocker Use With Less Prevalent Joint Pain and Lower Opioid Requirement in People With Osteoarthritis. Arthritis Care Res (Hoboken). Jul. 2017;69(7):1076-1081.

* cited by examiner

*Primary Examiner* — Brenda L Coleman
*Assistant Examiner* — Madeline E Braun
(74) *Attorney, Agent, or Firm* — Lisa Mueller; Casimir Jones SC

(57) ABSTRACT

The present invention relates to pharmaceutical combination for use in the treatment of pain comprising low doses of a beta blocker and an NSAID, pharmaceutical compositions comprising the combination and processes for preparation of the same. The present invention provides a pharmaceutical combination for use in the therapeutic treatment of pain comprising a non-selective NSAID and a low dose of beta blocker.

5 Claims, 1 Drawing Sheet

Hot Plate Test Results
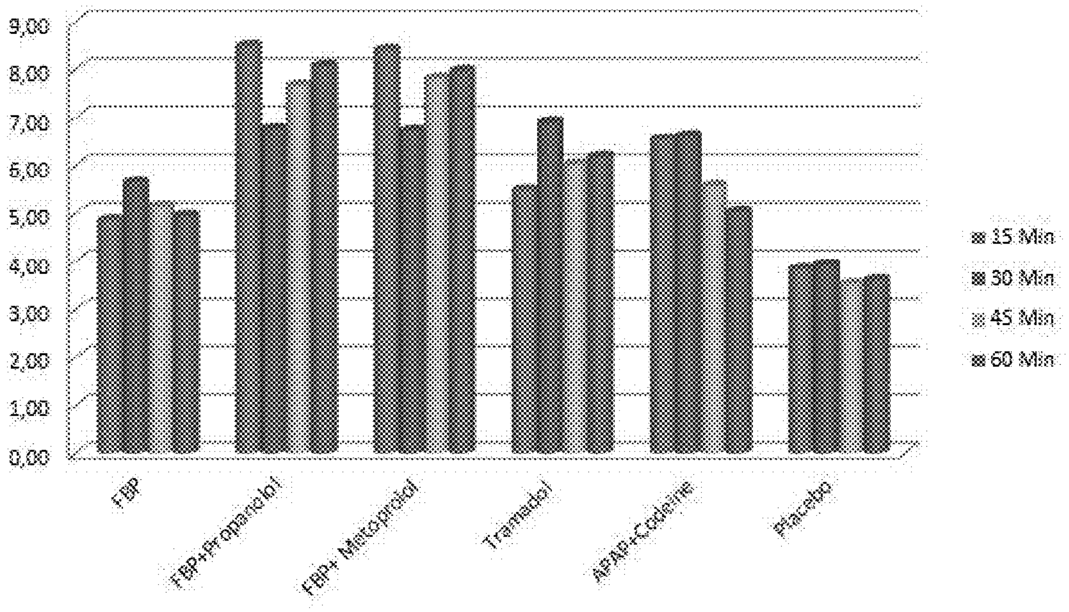

PHARMACEUTICAL COMBINATIONS FOR THE TREATMENT OF PAIN

TECHNICAL FIELD

The present invention relates to pharmaceutical combinations for use in the treatment of pain comprising a beta blocker and an NSAID; pharmaceutical compositions and processes thereof.

BACKGROUND ART

In general, pain can be divided into chronic pain and acute pain. Chronic pain is a sort of pain that is ongoing and usually lasts longer than six months. The definition of chronic pain can be both pain lasting longer than three months or pain present for most days over the past six months. This type of pain can continue even after the injury or illness causing pain after the injury or illness has already healed. Pain signals remain active in the nervous system for weeks, months, or years. Some people suffer chronic pain even when there is no past injury or apparent body damage.

Main types of chronic pain are nociceptive pain, somatic pain, visceral pain, neuropathic pain, psychogenic pain and idiopathic pain. Chronic pain is well described in the book "Classification of chronic pain descriptions of chronic pain syndromes and definitions of pain terms, Second Edition" prepared by Task Force on Taxonomy of the International Association for the Study of Pain. This type of pain can be caused by nerve damage, arthritis, cancer, fibromyalgia, osteoarthritis and psychological factors.

On the other hand, acute pain usually comes suddenly and is caused by a specific disease or injury. Acute pain types are listed in the "Clinical Pain Management Second Edition: Acute Pain" by Pamela Macintyre, David Rowbotham and Suellen Walker. Acute pain is often categorized by its cause or location.

Categorization of pain as acute and chronic is one of the several ways to categorize pain. Another categorization includes the type of nociceptive and neuropathic pain. Firstly, nociceptive pain can be somatic or visceral. Somatic pain is caused by an injury to the outer body part such as muscle, bone or skin. Contrary, visceral pain occurs when internal organs of the body are injured or inflamed. Secondly, neuropathic pain is caused by damage in the nerves.

Pain can also be categorized based on the intensity; pain intensity is frequently measured on an 11-point pain intensity numerical rating scale (PI-NRS), where 0 equals no pain and 10 equals the worst possible pain. According to the PI-NRS classification scheme for pain 0-2 is classified as mild, 3-5 is moderate, and 6-10 is severe.

There are many drugs that are known to be useful in the treatment of pain, which can be exemplified as NSAIDs, COX-2 inhibitors, opioids, steroids, antidepressants and gabapentinoids. NSAIDs and opioids are the most frequently used pain relief compounds. NSAIDs are generally used for the mild to moderate pain treatment while opioids are used in the treatment of moderate to severe pain. Opioids have a stronger analgesic effect compared to NSAIDs through their action on morphinic receptors. Therefore, they are also known as morphinic derivatives.

Although opioids are very effective in the treatment of pain, they are associated with some serious side effects which limit their use. These side effects include cognitive impairment, constipation, decreased sexual dysfunction, nausea, vomiting, sedation, somnolence and orthostatic hypotension. In addition, opioids demonstrate severe adverse effects such as addiction and opioid induced respiratory depression. Especially the addiction is one of the main problems for people using opioid based compounds. The opioid-induced respiratory depression is on the other hand, the primary cause of death following illicit or prescription opioid misuse. Fatal opioid overdose accounted for over 140 deaths a day in the USA in 2016 according to National Institutes of Health.

Non-Steroidal Anti-Inflammatory Drugs (NSAIDs) are a diverse group of compounds that are mainly used for the treatment of mild to moderate pain. They are also used to reduce fever and inflammation. They exert their pharmacological action by inhibiting the synthesis of prostaglandins (PGs) by non-selectively blocking cyclooxygenases 1 and 2 (COX-1 and COX-2) or by selectively blocking COX-2. Inhibition of COX-1 is also responsible, in part, for gastrointestinal side effects, which are the most frequent side effects of NSAIDs. Thus, the classification system of NSAIDs is based on their chemical structure and whether they inhibit the COX-1 and/or COX-2 enzymes.

The severity of side effects increases when NSAIDs or opioids are used in higher doses. In the prior art, there are a lot of studies aiming to limit the dose of analgesic compounds including NSAIDs and opioids, while providing an efficient pain management.

Some of these studies concentrated to combine NSAIDs with other pharmaceutical drugs to provide the treatment or prophylaxis of pain. For example, EP2175861B1 discloses a pharmaceutical combination comprising an NSAID and a prostaglandin for the treatment of pain wherein the effect of the NSAID is augmented. However the main effect of this combination is the reduction of gastrointestinal side effects caused by the use of NSAID. In the prior art, combinations of NSAIDs are generally focused on lowering the NSAIDs' side effects.

In addition, EP1011658B1 discloses a novel combination of NSAID and anti-epileptic compounds showing an improved reduction in the frequency and severity of pain while reducing the incidence of unwanted side effects caused by the higher doses of a single agent. However, antiepileptic drugs could have serious adverse effects influencing generally the central nervous system and it is known that these effects are often dose-dependent.

Furthermore, ibuprofen which is one of the most frequently used NSAID can be combined with acetaminophen (paracetamol) for the treatment of pain as disclosed in the study of Merry et al. (Combined acetaminophen and ibuprofen for pain relief after oral surgery in adults: a randomized controlled trial, Br J Anaesth. 2010 January). In the study, it is also disclosed that NSAIDs are commonly prescribed with acetaminophen. However, the required daily dose of this combination for obtaining a sufficient relief of pain is rather high and the frequency and intensity of side effects are increased accordingly.

Therefore, there still exists a particular need for providing an enhanced therapeutic treatment of pain with a significant efficiency and in the meantime reducing the side effects and providing a good safety profile.

BRIEF DESCRIPTION OF THE INVENTION

The present invention provides a synergistic drug combination comprising an NSAID or a pharmaceutically acceptable salt thereof and a beta blocker or a pharmaceutically acceptable salt thereof for use in the therapeutic treatment of pain.

In one embodiment of the present invention, a pharmaceutical combination for use in the therapeutic treatment of pain is provided which comprises;

- a) a non-selective NSAID selected from the group consisting of flurbiprofen, diclofenac, meloxicam, naproxen, ibuprofen, dexketoprofen, piroxicam, tenoxicam and pharmaceutically acceptable salts and/or derivatives thereof, and
- b) a beta blocker selected from metoprolol, propranolol, nebivolol, atenolol, betaxolol, bisoprolol, carvedilol or pharmaceutically acceptable salts and/or derivatives thereof.

In another embodiment, in the above described use the daily dose of beta blocker is 4 to 80 mg, preferably 6 to 70 mg, more preferably 8 to 60 mg.

In one embodiment of the present invention, a pharmaceutical combination for use in the therapeutic treatment of pain is provided which comprises an NSAID selected from the group consisting of flurbiprofen, diclofenac, meloxicam, naproxen, ibuprofen; and metoprolol or propranolol as a beta blocker, wherein the daily dose of beta blocker is 4 to 80 mg, preferably 6 to 70 mg, more preferably 8 to 60 mg.

In another embodiment of the present invention a pharmaceutical combination for use in the treatment of pain is provided which comprises;

- a) a non-selective NSAID selected from the group consisting of flurbiprofen, diclofenac, meloxicam, naproxen and ibuprofen, and
- b) a beta blocker selected from the group consisting of metoprolol, propranolol, nebivolol, atenolol, betaxolol, bisoprolol and carvedilol, wherein the daily dose of beta blocker is 4 to 80 mg, preferably 6 to 70 mg, more preferably 8 to 60 mg.

In one embodiment of the present invention, the pain is moderate to severe pain.

In another embodiment of the present invention the pain is muscle pain, joint pain, eye pain, orofacial pain, abdominal pain, gynecological pain, tissue or skin pain, inflammatory pain, pain resulting from osteoarthritis or rheumatoid arthritis, pain resulting from inflammatory bowel disease, bone pain, back pain, gout pain, allodynia, dysmenorrhea, headache, cluster headache, migraine pain, tendon pain, postoperative pain, post-stroke pain, cancer pain, dental pain, diabetic neuropathy, dysmenorrhea pain, stump pain, phantom pain, neuralgias, neuronitis, neuritis, AIDS-related neuropathy, MS-related neuropathy or spinal cord injury-related pain.

In another embodiment of the present invention a fixed unit dose pharmaceutical composition for use in the therapeutic treatment of pain is provided wherein the composition comprises a pharmaceutical combination according to the invention.

BRIEF DESCRIPTION OF THE DRAWINGS

The FIGURE is a bar graph showing the results of the hot plate test, presenting the latency in seconds measured 15, 30, 45 and 60 minutes after administration for furbiprofen (FRP), flurbiprofen in combination with propranolol, flurbiprofen in combination with metoprolol, tramadol, paracetamol in combination with codeine, and placebo.

DETAILED DESCRIPTION OF THE INVENTION

The present invention relates to a synergistic drug combination comprising an NSAID and a beta-blocker or a pharmaceutically acceptable salts and/or derivatives thereof for use in the therapeutic treatment of pain.

It has been surprisingly found that when NSAID is combined with a beta blocker, beta blocker acts synergistically with the NSAID and produces a much greater reduction in pain than when the NSAID is administered alone, even with low doses of beta blocker. In addition, the pharmaceutical combination of the present invention provides an effective treatment of pain with a reduced side effect profile compared to a treatment with an opioid receptor agonist with a large number of side effects and also providing a surprisingly superior level of analgesic effects compared to the combinations found in the prior art, even whilst employing a much lower dose of a beta blocker.

In one embodiment, the present invention provides a pharmaceutical combination comprising an NSAID and a beta blocker for use in the treatment of pain wherein the combination administered concomitantly, simultaneously, and separately or sequentially to the patient in need thereof.

As used herein, the term "therapeutic treatment" means treatment for a subject already having the disease, by administering to the subject the therapeutically effective amount of the composition of the present invention. Thus, the present invention is about the therapeutic treatment and relief of pain while the pain is already present in the subject who is to be administered the drug combination or the composition of the present invention.

The term "treatment" as used herein essentially means the cure, amelioration or improvement of a disease, pathological condition or disorder.

The term "pharmaceutically acceptable salt" as used herein essentially means the organic or inorganic salts of the active ingredient, in that case NSAID or beta blocker, including inorganic or organic acid addition salts of the active ingredient, exhibiting minimal or no undesired toxicological effects.

The term "derivative(s)" as used herein essentially means a compound which is formed by a chemical process from a parent compound, wherein the chemical formula of the parent compound is present in the derivative.

The term "subject" or "patient" as used herein is equivalent to a mammal in need of a treatment for a pain and could be a living human or an animal such as cat, dog and cattle.

The classification system of NSAIDs is based on their chemical structure and whether they inhibit the COX-1 and/or COX-2 enzymes: 2-Arylpropionic acids group, salicylates group, arylalkanoic acids group and oxicams group. Although there are more than these 4 groups, the preferred embodiment of the present invention is focused on these 4 groups of Non-selective (equipotent) COX inhibitors based on their ability to inhibit both the COX-1 and COX-2 enzymes, and there is also a group classified as selective COX-2 inhibitors, which would not be ideally used within the combination of the present invention, due to the serious risk of cardiovascular side effects. Thus, not to limit the scope of the present invention, the preferred embodiment of the present invention would include the use of a non-selective COX inhibitor/NSAID rather than a COX-2 inhibitor NSAID which have serious cardiovascular side effects.

Non-selective NSAIDs have a completely different mechanism of action compared to opioid medication interacting with opioid receptors. By using NSAIDs, the treatment of moderate to severe pain is provided and the use of opioids with serious addiction properties is eradicated.

In one embodiment of the present invention, NSAID is selected from the group consisting of 2-Arylpropionic acids group including alminoprofen, benoxaprofencarprofen, dexibuprofen, dexketoprofen, fenbufen, fenoprofen, flunoxaprofen, flurbiprofen, ibuprofen, ibuproxam, indoprofen, ketoprofen, ketorolac, loxoprofen, naproxen, oxaprozin, pirprofen, suprofen, tiaprofenic acid; salicylates group including alicylamide, salicyl salicylate, methyl salicylate, magnesium salicylate, faislamine, ethenzamide, diflunisal, choline magnesium salicylate, benorylate/benorilatem and amoxiprin, aspirin; arylalkanoic acids group including aceclofenac, acemetacin, alclofenac, bromfenac, diclofenac, etodolac, indometacin, nabumetone, oxametacin, proglumetacin, sulindac, and tolmetinor; and oxicams group including droxicam, lomoxicam, meloxicam, piroxicam, tenoxicam and pharmaceutically acceptable salts and derivatives thereof and their combinations.

In one embodiment of the present invention, NSAID is a non-selective COX inhibitor which is selected from the group consisting of ibuprofen, flurbiprofen, diclofenac, naproxen, meloxicam, piroxicam, acetyl salicylic acid, ketoprofen, dexketoprofen, ketorolac, lornoxicam, tenoxicam and pharmaceutically acceptable salts and/or derivatives thereof; preferably flurbiprofen, ibuprofen, diclofenac, dexketoprofen, piroxicam, tenoxicam, naproxen, meloxicam and more preferably flurbiprofen, ibuprofen, diclofenac, naproxen, meloxicam and pharmaceutically acceptable salts and/or derivatives thereof.

In one embodiment of the present invention, the pharmaceutical combination comprises a beta blocker wherein the daily dose is 4 to 80 mg, preferably 6 to 70 mg, more preferably 8 to 60 mg.

The present invention has surprisingly demonstrated that lower doses of beta blockers are significantly effective for the treatment of pain when combined with NSAIDs, compared to the beta blocker doses used in the prior art for their conventional purposes. Thus, side effects occurred while using beta blockers are decreased and high potency are provided.

Beta blockers are a class of drugs used in the management of high blood pressure, heart rhythms and heart failure. As they are about heart failure or blood pressure treatment, these drugs can be used with higher doses or even with extra doses. But, they cause side effects including impotence, hallucinations, breathlessness, lightheadedness and memory loss. And, while their doses become higher, these side effects are increasing in prevalence.

Daily dose of beta-blockers are at least the half of daily dose used in the prior art for patients using beta blockers for other conventional uses for the treatment of cardiological conditions as described in the present invention or as known by the person with ordinary skill in the art. In addition, beta-blockers have a very well known safety profile. Now, while they are used at lower doses for the treatment of pain, the present invention provides better safety profile by limiting the possible side effects such as bronchospasms and by enabling their use on an expended patient population that are already administered other cardio protective and/or anti-hypertensive medications or ones that suffer from asthma/COPD as well.

In other words, the challenge during the development of the present invention, was to decrease the dose of the beta blocker as much as possible, whilst obtaining a potent analgesic effect, in order to create the possibility of the administration of the combination of the present invention for the treatment of pain, to the broadest possible patient population including those suffering from hypertension, asthma and/or COPD, even if they are taking another medicament including beta blockers for their conventional use.

Accordingly, in the preferred embodiment of the present invention; the minimum and maximum daily dose of the beta blockers used in the combination of the present invention is less than half of their doses approved for conventional uses by the U.S. FDA. daily doses of the present invention are disclosed in the Table below:

| | Minimum Daily Dosage when used in fixed dose combination with an NSAID for the treatment of pain | Maximum Daily Dosage when used in fixed dose combination with an NSAID for the treatment of pain |
|---|---|---|
| Alprenolol | 10 mg | 100 mg |
| Acebutolol | 10 mg | 100 mg |
| Atenolol | 1 mg | 30 mg |
| Betaxolol | 1 mg | 10 mg |
| Bisoprolol | 1 mg | 7.5 mg |
| Carteolol | 1 mg | 3 mg |
| Carvedilol | 1 mg | 20 mg |
| Labetolol | 20 mg | 100 mg |
| Nadolol | 20 mg | 80 mg |
| Oxprenolol | 5 mg | 60 mg |
| Penbutolol | 5 mg | 30 mg |
| Pindolol | 5 mg | 20 mg |
| Propranolol | 1 mg | 80 mg |
| Sotolol | 5 mg | 80 mg |
| Timolol | 1 mg | 20 mg |
| Metoprolol | 1 mg | 80 mg |
| Esmolol | 30 mg | 200 mg |
| Nebivolol | 1 mg | 10 mg |

In one embodiment of the present invention, beta blocker is beta-1 selective beta blocker, beta-2 selective beta blocker, alpha-1/beta adrenergic antagonists, beta-3 selective beta blocker, beta-1 and beta-3 selective beta blocker and/or non-selective beta blocker (beta-1 and beta-2 selective beta-blocker or a mixture of two or more beta-blockers. Beta-1 selective beta blocker is selected from the group consisting of acebutolol, atenolol, betaxolol, bisoprolol, celiprolol, esmolol, metoprolol, nebivolol and pharmaceutically acceptable salts and derivatives thereof and their combinations. Non-selective beta blocker is selected from the group consisting of alprenolol, bucindolol, carteolol, levobunolol, medroxalol, mepindolol, metipranolol, nadolol, oxprenolol, penbutolol, pindolol, propafenone (propafenone is a sodium channel blocking drug that is also a beta-adrenergic receptor antagonist), propranolol, sotalol, timolol and pharmaceutically acceptable salts and derivatives thereof and their combinations. The beta blocker may also have an intrinsic sympathomimetic activity as acebutolol, betaxolol, carteolol, carvedilol, labetalol, oxprenolol, penbutolol, pindolol.

In one embodiment of the present invention, beta blocker is selected from the group consisting of acebutolol, atenolol, betaxolol, propranolol, bisoprolol, celiprolol, esmolol, metoprolol, nebivolol and pharmaceutically acceptable salts and derivatives thereof; preferably metoprolol, propranolol, nebivolol, atenolol, betaxolol, bisoprolol, carvedilol and pharmaceutically acceptable salts and derivatives thereof.

In one preferred embodiment the pharmaceutical combination of the present invention comprises NSAID or its pharmaceutically acceptable salt and/or derivatives thereof wherein when the NSAID is flurbiprofen, the daily dose is between 40 to 300 mg, when the NSAID is diclofenac, the daily dose is between 20 to 220 mg, when the NSAID is meloxicam, the daily dose is between 6 to 30 mg, when the NSAID is naproxen, the daily dose is between 200 to 1300 mg and when the NSAID is ibuprofen, the daily dose is between 400 to 3200 mg.

In one embodiment, the present invention provides a pharmaceutical combination for use in the therapeutic treatment of pain which comprises;

a) a non-selective NSAID selected from the group consisting of flurbiprofen, diclofenac, meloxicam, naproxen, ibuprofen, dexketoprofen, piroxicam, tenoxicam and pharmaceutically acceptable salts and/or derivatives thereof, b) a beta-blocker or a pharmaceutically acceptable salts thereof selected from the group consisting of metoprolol, propranolol, nebivolol, atenolol, betaxolol, bisoprolol, carvedilol and pharmaceutically acceptable salts and/or derivatives thereof.

In one embodiment, the present invention provides a pharmaceutical combination for use in the therapeutic treatment of pain which comprises;

a) a non-selective NSAID selected from the group consisting of flurbiprofen, diclofenac, meloxicam, naproxen, ibuprofen, dexketoprofen, piroxicam, tenoxicam and pharmaceutically acceptable salts and/or derivatives thereof, and b) a beta blocker selected from metoprolol, propranolol, nebivolol, atenolol, betaxolol, bisoprolol, carvedilol or pharmaceutically acceptable salts and/or derivatives thereof, wherein the daily dose of beta blocker is 4 to 80 mg, preferably 6 to 70 mg, more preferably 8 to 60 mg, and preferably wherein when, said beta blocker is propranolol, the daily amount is between 8 to 50 mg, when, said beta blocker is metoprolol, the daily amount is between 5 to 45 mg, when, said beta blocker is carvedilol, the daily amount is between 2 to 15 mg, when, said beta blocker is bisoprolol, the daily amount is between 1 to 5 mg, In one embodiment, non-selective NSAID is selected from the group consisting of flurbiprofen, diclofenac, meloxicam, naproxen, ibuprofen and pharmaceutically acceptable salts and/or derivatives thereof.

In one embodiment, the present invention provides a pharmaceutical combination for use in the therapeutic treatment of pain which comprises;

a) a non-selective NSAID selected from the group consisting of flurbiprofen, diclofenac, meloxicam, naproxen, ibuprofen and pharmaceutically acceptable salts and/or derivatives thereof, and b) a beta blocker selected from metoprolol, propranolol, nebivolol, atenolol, betaxolol, bisoprolol, carvedilol or pharmaceutically acceptable salts and/or derivatives thereof;

wherein when the NSAID is flurbiprofen, the daily dose is between 40 to 300 mg, when the NSAID is diclofenac, the daily dose is between 20 to 220 mg, when the NSAID is meloxicam, the daily dose is between 6 to 30 mg, when the NSAID is naproxen, the daily dose is between 200 to 1300 mg and when the NSAID is ibuprofen, the daily dose is between 400 to 3200 mg.

In the most preferred embodiment the pharmaceutical combination of the present invention comprises metoprolol, propranolol or their pharmaceutically acceptable salts and/or derivatives thereof wherein the daily dose of metoprolol or propranolol is between 4 to 80 mg, 6 to 70 mg or 8 to 60 mg and preferably 3 to 60 mg and preferably 3 to 50 mg. More preferably, the daily dose of metoprolol or propranolol is 3 to 45 mg.

According to the present invention, the most preferred pharmaceutical combinations for use in the treatment of pain are as follows:

metoprolol in combination with flurbiprofen,
metoprolol in combination with naproxen,
propranolol in combination with flurbiprofen, and
propranolol in combination with naproxen,
metoprolol in combination with diclofenac
metoprolol in combination with meloxicam,
propranolol in combination with diclofenac, and
propranolol in combination with meloxicam, The pain treated with the use of the combination of the present invention may be moderate to severe pain and/or chronic or acute pain and/or nociceptive or neuropathic pain. The pain is preferably moderate to severe pain. In one aspect, the present invention provides a pharmaceutical combination for the therapeutic treatment of moderate to severe pain without any addiction.

In one embodiment, said pain is a muscle pain, joint pain, eye pain, orofacial pain, abdominal pain, gynecological pain, tissue or skin pain, inflammatory pain, pain resulting from osteoarthritis or rheumatoid arthritis, pain resulting from inflammatory bowel disease, bone pain, back pain, gout pain, fibromyalgia, allodynia, dysmenorrhea, headache, cluster headache, migraine pain, tendon pain, postoperative pain, post-stroke pain, cancer pain, dental pain, diabetic neuropathy, dysmenorrhea pain, stump pain, phantom pain, neuralgias, neuronitis, neuritis, AIDS-related neuropathy, MS-related neuropathy or spinal cord injury-related pain.

More preferably, said pain is muscle pain, back pain, post-operative pain, headache, dysmenorrhea, cluster headache, cancer pain or migraine pain.

In one embodiment, the pain is preferably chronic pain.

In a preferred embodiment, the combination of the present invention is used for the treatment of moderate to severe chronic or acute nociceptive pain or migraine pain; preferably moderate to severe chronic or acute somatic or visceral pain or migraine pain; more preferably moderate to severe chronic or acute visceral pain. Somatic pain is selected from the group consisting of muscle pain, bone pain, tendon pain or skin pain.

In another embodiment, the present invention provides a therapeutic drug combination comprising an NSAID and a beta blocker for simultaneous administration or a pharmaceutical composition comprising the drug combination according to the present invention in a fixed unit dosage form for use in the therapeutic treatment of pain.

The term "fixed unit dosage form" as used herein means a single dosage unit comprising a combination of two or more active ingredients with pharmaceutically acceptable excipient(s), in that case NSAID and beta blocker.

The term "simultaneous" as used herein means that 2 active ingredients, in that case NSAID and beta blocker are administered at the same time and by the same route.

The term "concomittant administration" or "concomitantly" as used herein; means administration of a NSAID or beta blocker within a one hour time frame or when provided as a treatment package where both active compounds are given for administration in a single treatment package, provided in separate dosage units but inside the same pack for the treatment of pain.

In another embodiment of the present invention, a fixed unit dose pharmaceutical composition for use in the therapeutic treatment of pain is provided wherein the composition comprises a pharmaceutical combination which comprises;

a) a non-selective NSAID selected from the group consisting of flurbiprofen, diclofenac, meloxicam, naproxen, ibuprofen, dexketoprofen, piroxicam, tenoxicam and pharmaceutically acceptable salts and/or derivatives thereof, and b) a beta blocker selected from metoprolol, propranolol, nebivolol, atenolol, betaxolol, bisoprolol, carvedilol or pharmaceutically acceptable salts and/or derivatives thereof, wherein the amount of beta blocker in the composition is preferably in the range of from 1 to 20 mg and preferably 3 to 15 mg.

In another embodiment of the present invention a fixed unit dose pharmaceutical composition for use in the therapeutic treatment of pain is provided wherein the composition comprises a pharmaceutical combination which comprises;

a) a non-selective NSAID selected from the group consisting of flurbiprofen, diclofenac, meloxicam, naproxen, ibuprofen and pharmaceutically acceptable salts and/or derivatives thereof, and b) a beta blocker selected from metoprolol, propranolol, nebivolol, atenolol, betaxolol, bisoprolol, carvedilol or pharmaceutically acceptable salts and/or derivatives thereof;

wherein the amount of beta blocker in the composition is preferably in the range of from 1 to 20 mg and preferably 3 to 15 mg.

In one embodiment of the present invention, beta blocker is preferably metoprolol or propranolol.

In one preferred embodiment the fixed unit dose pharmaceutical composition of the present invention comprises NSAID or its pharmaceutically acceptable salt thereof, wherein when used in a fixed unit dose pharmaceutical composition, said NSAID is flurbiprofen, the amount is between 40 to 220 mg, when said NSAID is diclofenac, the amount is between 10 to 110 mg, when said NSAID is meloxicam, the amount is between 3 to 17 mg, when said NSAID is naproxen, the amount is between 200 to 600 mg and when said NSAID is ibuprofen, the amount is between 400 to 800 mg.

In one embodiment of the present invention, a fixed unit dose pharmaceutical composition for use in the therapeutic treatment of pain is administrated 1 to 4 times daily.

In one embodiment of the present invention, a fixed unit dose pharmaceutical composition for use in the therapeutic treatment of pain is provided wherein the composition comprises a pharmaceutical combination which comprises;

a) a non-selective NSAID selected from the group consisting of flurbiprofen, diclofenac, meloxicam, naproxen, ibuprofen, dexketoprofen, piroxicam, tenoxicam and pharmaceutically acceptable salts and/or derivatives thereof, b) a beta blocker selected from metoprolol, propranolol, nebivolol, atenolol, betaxolol, bisoprolol, carvedilol or pharmaceutically acceptable salts and/or derivatives thereof, and c) at least one pharmaceutically acceptable excipient.

In one embodiment, the fixed unit dosage form of the present invention may be an oral dosage form. This oral dosage form may be tablet, capsule, gel capsule, pellet, granule, tablet in tablet, tablet in capsule, powder, cachet, troche, caplet or coated tablet, preferably being tablet, capsule or powder. The pharmaceutical composition may also be in the form of drop, pellet, granule, aerosol, mouth wash, gargle, inhalable particle, inhalable solution, emulsion, lotion, solution, suspension, syrup, powder, transdermal patch, impregnated dressing, cream, ointment, gel, foam, paste, spray, suppository, ocular and injectable. Furthermore, the pharmaceutical composition may comprise pulsatile, sustained, delayed or controlled release, immediate or modified release mode of action.

The injectable dosage form may be powder to be mixed with water or another solvent for injection or liquid for injection and the dosage form may be administered as IM,IV and subcutaneously and preferably as IV.

The transdermal dosage form may be a topical preparation or a patch that can deliver the active ingredients of the composition to the blood stream of the subject.

In another embodiment of the present invention, the pharmaceutical composition further comprises at least one pharmaceutically acceptable excipient such as a carrier. Fixed dosage forms of the present invention may comprise suitable solvents, water, fillers, diluents, binders, lubricants, disintegrating agents, surfactants, glidants, sweetening agents, disaggregators, coloring agents and coating agents as pharmaceutically acceptable excipients and preferably disintegrants, lubricants and mixtures thereof.

Pharmaceutically acceptable diluents of the present invention may be selected from magnesium stearate, lactose, microcrystalline cellulose, starch, pre-gelatinized starch, calcium phosphate, calcium sulphate, calcium carbonate, sodium starch glycolate, mannitol, sorbitol, xylitol, sucrose, maltose, fructose, dextrose and the like or mixtures thereof.

Pharmaceutically acceptable binders of the invention may be selected from starches, natural sugars, corn sweeteners, natural and synthetic gums, cellulose derivatives such as hydroxypropyl cellulose, hydroxypropyl methylcellulose, microcrystalline cellulose, gelatin, polyvinylpyrrolidone, polyethylene glycol, waxes, sodium alginate, alcohols, water and the like or mixtures thereof.

Pharmaceutically acceptable lubricants of the present invention may be selected from metallic stearates, metallic lauryl sulfates, fatty acids, fatty acid esters, fatty alcohols, paraffin, hydrogenated vegetable oils, polyethylene glycols, boric acid, polyvinylpyrrolidone, sodium benzoate, sodium acetate, sodium chloride, talk and the like or mixtures thereof; preferably metallic stearates or fatty acid esters including glyceryl monostearate, glyceryl tribehenate, glyceryl dibehenate and glyceryl stearate are used.

Pharmaceutically acceptable disintegrating agents of the present invention may be selected from starches, cellulose derivatives, polyvinylpyrrolidone, crospovidone, clays, ion-exchange resins, alginic acid, sodium alginate and the like or mixtures thereof;

Pharmaceutically acceptable surfactants of the present invention may be selected from sulfates, sulfonates, phosphates, carboxylates, primary-secondary-tertiary amines, quaternary ammonium compounds, fatty alcohols, sugar esters of fatty acids, glycerides of fatty acids, polyoxy ethylene glycol alkyl ethers, polisorbates, sorbitan alkyl esters, poloxamers and the like or mixtures thereof.

Pharmaceutically acceptable glidants of the present invention may be selected from silicon dioxide, magnesium trisilicate, starch, talc, colloidal silicon dioxide, silicon hydrogel and the like or mixtures thereof.

EXAMPLES

The present invention will be explained more in detail by illustrating Examples and study.

Example 1

The following composition provides the contents of an embodiment of the present invention. The composition is in the form of a film tablet comprising flurbiprofen and propranolol hydrochloride.

| Flurbiprofen/Propranolol hydrochloride 100 mg/10 mg Film Tablet | |
|---|---|
| Unit Formula Ingredients | mg/tb. |
| Flurbiprofen | 100.00 |
| Propranolol hydrochloride | 10.00 |
| Hydroxypropyl cellulose | 20.00 |
| Microcrystalline Cellulose type 101 | 100.00 |
| Crospovidone | 40.00 |
| Microcrystalline Cellulose type 102 | 40.00 |
| Colloidal silicon dioxide | 2.50 |
| Magnesium Stearate | 5.00 |
| Weight of Core Tablet | 327.50 |
| Aquarius ™ Preferred HSP Orange | 15 |
| Weight of Coated Tablet | 332.50 |

Manufacturing Directions (Wet Granulation)

1. Sieve together Flurbiprofen, Propranolol, microcrystalline cellulose type 101 and hydroxypropylcellulose,
2. Granulate the mixture of step 1 with granulation solution prepared by distillated water and crospovidone (15 mg) in high shear granulator
3. Dry the mixture in fluid-bed granulator and pass through a 0.8-mm sieve,
4. Add microcrystalline cellulose type 102, crospovidone (25 mg) and mix 15 minutes.
5. Add magnesium stearate to the mixture and mix 3 minutes.
6. Compress tablets,
7. Coat tablets with coating solution (Preferred HSP orange)

| Diclofenac Potassium/Metoprolol tartrate 50 mg/10 mg Film Tablet | |
|---|---|
| Unit Formula Ingredients | mg/tb. |
| Diclofenac potassium | 50.00 |
| Metoprolol tartrate | 10.00 |
| Lactose Granule | 28.00 |
| Microcrystalline Cellulose type 102 | 67.00 |
| Hydroxypropyl cellulose | 8.00 |
| Crospovidone | 10.00 |
| Colloidal silicon dioxide | 2.00 |
| Magnesium Stearate | 2.00 |
| Weight of Core Tablet | 177.00 |
| Aquarius ™ Preferred HSP BPP316041 Green | 7 |
| Weight of Coated Tablet | 184.00 |

Manufacturing Directions (Direct Compression)

1. Sieve Diclofenac potassium, lactose granule, hydroxypropyl cellulose and mix 10 min
2. Add Metoprolol and microcrystalline cellulose and mix 10 min
3. Add crospovidone and mix 5 min
4. Sieve colloidal silicone dioxide and microcrystalline cellulose together and mix 5 min
5. Add magnesium stearate to the mixture and mix 3 minutes.
6. Compress tablets,
7. Coat tablets with coating solution (Preferred HSP BPP316041 Green)

Pivotal Hot Plate Test Study

Flurbiprofen, propranolol and metoprolol are all well-established drugs from their respective classes and were used in this study on purpose to test the analgesic effect of the combination of a non selective COX inhibitor (flurbiprofen) with non-selective (propranolol) or beta-1 selective beta blocker (metoprolol).

Hot plate test of Eddy and Leimbach (1953) is a test of the pain response in animals and are well described in the study of Michael Williams, Roger D. Porsolt, in xPharm: The Comprehensive Pharmacology Reference, 2007.

In this study, a total of 28, 250±20 g in weight female Albino Wistar rats were used. The rats, were clinically healthy and they were fed ad libitum commercial rat feed and allowed to reach sterile reverse osmosis filtered water supply. Female rats were preferred as their higher degree nociceptive pain response than males (Craft et al. European Journal of Pain 8, 2004, 397-411). The animals were kept in polycarbonate universal rat cages. 12 hours light and 12 hours dark cycle were applied and environmental temperature was adjusted to 22±1° C. before the administration of the drugs as detailed below.

TABLE 2

| Treatment groups | | | | |
|---|---|---|---|---|
| Group Name | Rat Numbers | Drug and/or Drug Combinations as mg/kg with Hydroxypropyl cellulose (HPMC) as carrier(excipient) | | |
| FBP(Flurbiprofen) | 7 | Flurbiprofen 40 mg/kg | | HPMC 20 mg/kg |
| FBP + Propranolol | 7 | Flurbiprofen 40 mg/kg | Propranolol 4 mg/kg | HPMC 20 mg/kg |
| FBP + Metoprolol | 7 | Flurbiprofen 40 mg/kg | Metoprolol 5 mg/kg | HPMC 20 mg/kg |
| Tramadol | 7 | Tramadol 25 mg/kg | — | HPMC 20 mg/kg |
| Paracetamol (APAP) + Codeine | 7 | Paracetamol 200 mg/kg | Codein 20 mg/kg | HPMC 20 mg/kg |
| Placebo | 7 | HPMC 30 mg/kg | — | |

Drug and drug combinations in oral fixed dose powder form were diluted with distilled water to be administered by gavage to all the experimental groups. Treatment plan and drug doses were applied as indicated below.

In the experiment, the compositions at the doses specified in Table 3 with 20 mg/kg of HPMC are administered to all 5 groups with 7 rats in each through oral gavage.

Analgesic Effect

For the evaluation of pain relieving efficacy of the tested drugs, heat induced pain model was used. In this rat model; the analgesic activity was evaluated in rats by using hot plate (Analgesic hot plate, May AHP 0603) maintained at 52.5° C.±0.1° C. Each rat was placed on the bottom of the hot plate surrounded by 20 cm diameter round plastic chamber. The touch of the footpads of the animal was accepted as the starting time and equipped chronometer recording was synchronously started. Hot plate test ended by the observation of pain related behaviors such as paw licking, limb flicking and/or jumping and then heat induced pain tolerance time of each animal was calculated. Hot plate test was repeated at four different time points following drug or placebo administration at 15 min, 30 min, 45 min and 60 min. The total latency per group was divided to 7 to get an average latency in seconds per group. A cut-off time of 20 seconds was used to avoid tissue injury. FIG. 1 also shows the result of hot plate test demonstrating the latency in seconds.

TABLE 3

The results of the hot plate test demonstrating the latency in seconds

| | FBP | FBP + Propanolol | FBP + Metoprolol | Tramadol | APAP+ Codeine | Placebo |
|---|---|---|---|---|---|---|
| 15 Min | 4.87 | 8.50 | 8.41 | 5.49 | 6.54 | 3.84 |
| 30 Min | 5.65 | 6.77 | 6.73 | 6.90 | 6.61 | 3.93 |
| 45 Min | 5.15 | 7.67 | 7.81 | 6.03 | 5.57 | 3.53 |
| 60 Min | 4.96 | 8.07 | 7.97 | 6.19 | 5.04 | 3.61 |

Tail Flick Test

In the Tail Flick test, the rats were allocated individually in a restrainer that is allowing their tail free. Then, the tail of each rat was placed over a 0.5 cm diameter infrared heat source. The tail flicking reaction time (how long it takes for the rat to flick its tail when placed over a heat source) of the rat's was recorded 1 hour after oral administration of the test compounds (administered by gavage) with the same dosages as the hot plate study. The animals were restrained in transparent Plexiglas tubes during the measurement. The tests were performed 3 times (with a 15 sec interval) at the 60 minutes time point, and the average of the measurements was used. For this experiment, the automated Ugo Basile Tail Flick instrument was used.

TABLE 5

The tail flick results in seconds, 1 hour after administration.

| | FBP | FBP + Propranolol | FBP + Metoprolol | Tramadol | Paracetamol + Codeine | Placebo |
|---|---|---|---|---|---|---|
| 60 min | 4.95 sec | 10.06 sec | 9.71 sec | 5.81 sec | 6.46 sec | 2.21 sec |

Evaluation of the Results:

In the hot plate test; Flurbiprofen administered alone had the lowest analgesic effect compared to all the other groups except the placebo group. FBP+Prop combined drug exhibited statistically significant analgesic activity in the hot plate model by increasing the reaction time of the rats to over 8.0 sec both at 15 min and 60 min after treatment in comparison to control (placebo) which was below 4 sec at both time points. FBP+Metoprolol combined drug exhibited highly similar and efficient results as far as analgesic effect is concerned. Tramadol produced a heat induced pain reaction time of less than 7 sec in the same test at all of the time points. Tramadol showed its peak of activity at 30 min. The paracetamol+codeine group produced a reaction time of less than 7 sec in the same test at all of the time points, with a peak of activity at 30 min as well. The superiority of the compositions of the present invention with a superior analgesic effect is evident by the surprising results achieved, where the co-administration of a NSAID (flurbiprofen) and beta blockers (propranolol (non-selective beta blocker) and metoprolol (beta-1-selective beta blocker) and) and both had a peak activity at 15 minutes after administration and retain its superior analgesic activity throughout all the time points demonstrating a strong effect for pain relief. The only time point where FBP+Prop and FBP+Met were slightly lower efficacy than tramadol was at 30 minutes but there was no statistically significant difference between them. Most interestingly, pain tolerance time of FBP+Prop and FBP+Met treatment had their highest level at 15 min, while their 45 min and 60 min results were almost the same with 15 min. Thus the compositions of the present invention act both as a fast acting treatment modality and also as a longer acting modality for pain relief, which is also demonstrated in the tail flick test, which shows a significant difference between the FBP+Prop and FBP+Met groups and the others, including 2 well known opioids, 1 hour after the administration of the compositions. Most importantly, the dose of metoprolol and propranolol was at least half of their normal dose used for their conventional indications.

The invention claimed is:

1. A method of treating moderate to severe pain, the method consisting of administering to an individual having moderate to severe pain and in need of such treatment a pharmaceutical combination consisting of (a) a combination of drugs consisting of a beta blocker and a non-selective NSAID; and (b) one or more pharmaceutically acceptable excipients, wherein the combination of the beta blocker and non-selective NSAID are:

1) between 3 to 15 mg of metoprolol in combination with flurbiprofen;
2) between 3 to 15 mg of metoprolol in combination with naproxen;
3) between 3 to 15 mg of propranolol in combination with flurbiprofen;
4) between 3 to 15 mg of propranolol in combination with naproxen;
5) between 3 to 15 mg of metoprolol in combination with diclofenac;
6) between 3 to 15 mg of propranolol in combination with diclofenac; or
7) between 3 to 15 mg of propranolol in combination with meloxicam.

2. The method of claim 1, wherein the pain is muscle pain, joint pain, eye pain, orofacial pain, abdominal pain, gynecological pain, tissue or skin pain, inflammatory pain, pain resulting from osteoarthritis or rheumatoid arthritis, pain resulting from inflammatory bowel disease, bone pain, back pain, gout pain, fibromyalgia, allodynia, dysmenorrhea, headache, cluster headache, migraine pain, tendon pain, postoperative pain, post-stroke pain, cancer pain, dental pain, diabetic neuropathy, dysmenorrhea pain, stump pain, phantom pain, neuralgias, neuronitis, neuritis, AIDS-related neuropathy, MS-related neuropathy or spinal cord injury-related pain.

3. The method of claim 1, wherein the pain is muscle pain, back pain, post-operative pain, headache, dysmenorrhea, cluster headache, cancer pain or migraine pain.

4. A method of treating an individual suffering from moderate to severe pain, the method consisting of administering to an individual suffering from moderate to severe pain and in need of such treatment a fixed unit oral dosage form of a pharmaceutical composition, wherein the pharmaceutical composition consists of: (a) a combination of drugs consisting of a beta blocker and a non-selective NSAID; and (b) one or more pharmaceutically acceptable excipients, wherein the combination of the beta blocker and non-selective NSAID are:

1) 3 to 15 mg of metoprolol in combination with between 40 to 220 mg of flurbiprofen;
2) 3 to 15 mg of metoprolol in combination with between 200 to 600 mg of naproxen;
3) 3 to 15 mg of propranolol in combination with between 40 to 220 mg of flurbiprofen;
4) 3 to 15 mg of propranolol in combination with between 200 to 600 mg of naproxen;
5) 3 to 15 mg of metoprolol in combination with between 10 to 110 mg of diclofenac;
6) 3 to 15 mg of propranolol in combination with between 10 to 110 mg of diclofenac; or
7) 3 to 15 mg of propranolol in combination with between 3 to 17 mg of meloxicam.

5. The method of claim 4, wherein the oral dosage form is administrated 1 to 4 times daily.

* * * * *